(12) United States Patent
Nordgren et al.

(10) Patent No.: US 10,799,211 B2
(45) Date of Patent: Oct. 13, 2020

(54) STERILE COVERS FOR ULTRASOUND PROBE

(71) Applicant: CIVCO Medical Instruments Co., Inc., Kalona, IA (US)

(72) Inventors: Gregory Nordgren, North Liberty, IA (US); Bret Simon, West Liberty, IA (US); Hannah Marie Rundell, Coralville, IA (US)

(73) Assignee: CIVCO MEDICAL INSTRUMENTS CO., INC., Kalona, IA (US)

( * ) Notice: Subject to any disclaimer, the term of this patent is extended or adjusted under 35 U.S.C. 154(b) by 1099 days.

(21) Appl. No.: 14/982,288

(22) Filed: Dec. 29, 2015

(65) Prior Publication Data

US 2016/0192903 A1 Jul. 7, 2016

Related U.S. Application Data

(60) Provisional application No. 62/097,477, filed on Dec. 29, 2014.

(51) Int. Cl.
*A61B 8/00* (2006.01)
(52) U.S. Cl.
CPC .................. *A61B 8/4422* (2013.01)
(58) Field of Classification Search
CPC ................................................ A61B 8/4422
See application file for complete search history.

(56) References Cited

U.S. PATENT DOCUMENTS

| | | | |
|---|---|---|---|
| 3,920,179 A | * | 11/1975 | Hall .................. A61J 19/00 128/DIG. 24 |
| 4,593,699 A | | 6/1986 | Poncy et al. |
| 5,259,383 A | | 11/1993 | Holstein et al. |
| 5,605,009 A | * | 2/1997 | Elder ................ A01G 13/0281 47/32 |
| 5,910,113 A | | 6/1999 | Pruter |
| 6,123,080 A | | 9/2000 | Mohan et al. |

(Continued)

FOREIGN PATENT DOCUMENTS

| | | |
|---|---|---|
| JP | 61-172554 A | 8/1986 |
| JP | 2000171730 A | 6/2000 |

(Continued)

OTHER PUBLICATIONS

S.A. Lopez et al., "Design, prototyping and evaluation of a collapsible device for single-operator sheathing of ultrasound probes," Mech. Sci. 4, 1-7, 2013 doi:10.5194/ms-4-1-2013.

(Continued)

*Primary Examiner* — Christopher L Cook
(74) *Attorney, Agent, or Firm* — Snyder, Clark, Lesch & Chung, LLP

(57) ABSTRACT

Three embodiments of flexible covers for an ultrasound probe are disclosed. The first embodiment comprises a flexible sheath applied with a ring applicator and elastic bands. The second embodiment comprises a flexible sheath applied with a dual-walled foldable applicator. The third embodiment comprises a folded-over flexible sheath which is then rolled, incorporating in the roll a flexible band. Each of the embodiments is designed to facilitate easy application of a sterile sheath over an ultrasound probe.

4 Claims, 25 Drawing Sheets

(56) References Cited

U.S. PATENT DOCUMENTS

| | | | |
|---|---|---|---|
| 6,267,726 B1* | 7/2001 | Grimm | A61B 1/00142 |
| | | | 600/459 |
| 7,850,664 B1 | 12/2010 | Pruter | |
| 8,353,880 B1 | 1/2013 | Pruter | |
| 10,085,716 B2 | 10/2018 | Romano et al. | |
| 2003/0149366 A1 | 8/2003 | Stringer et al. | |
| 2007/0276253 A1* | 11/2007 | Park | A61B 8/00 |
| | | | 600/461 |
| 2009/0155341 A1 | 6/2009 | Gavriely et al. | |
| 2012/0008877 A1* | 1/2012 | Hunt | A61G 9/003 |
| | | | 383/6 |
| 2014/0053461 A1* | 2/2014 | Blaha | A01G 13/00 |
| | | | 47/20.1 |

FOREIGN PATENT DOCUMENTS

| | | |
|---|---|---|
| JP | 2011 072511 A | 4/2011 |
| JP | 2012130675 A | 7/2012 |
| WO | 2009077176 A1 | 6/2009 |
| WO | 2014163311 A1 | 10/2014 |

OTHER PUBLICATIONS

Protek Medical Products: "Probe Covers for Ultrasound", Dec. 31, 2013, pp. 1-6, Retrieved from the Internet: URL:http:/www.protekmedical.com/Images/pdf_brochure_probecovers2.pdf.
International Search Report for PCT/US2015/067838 dated May 4, 2016.

* cited by examiner

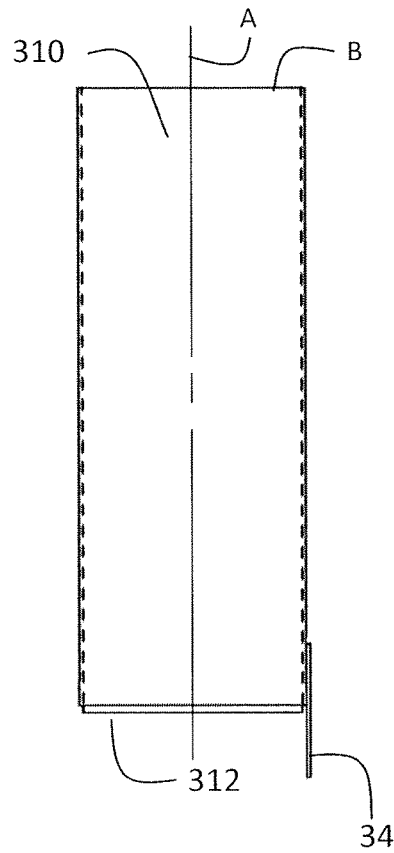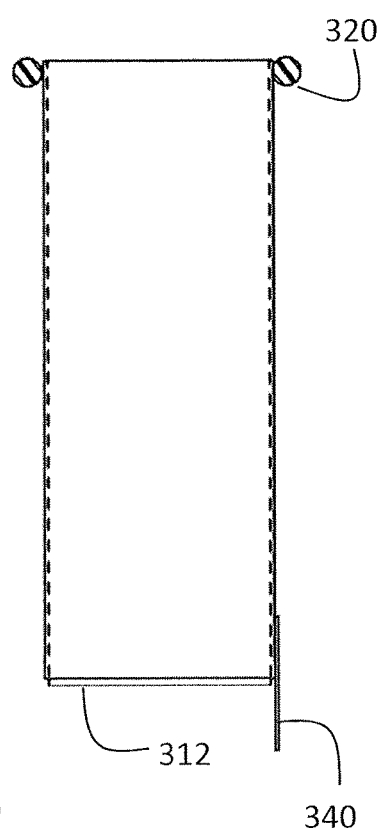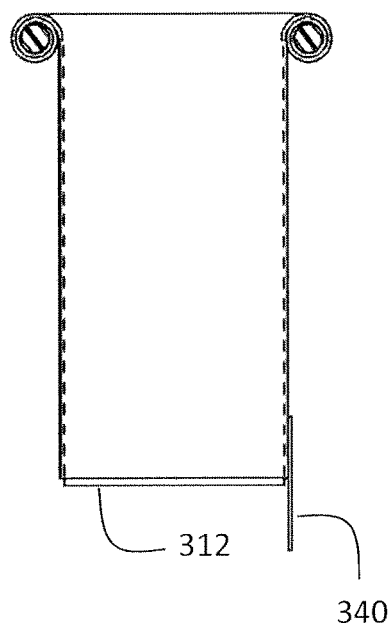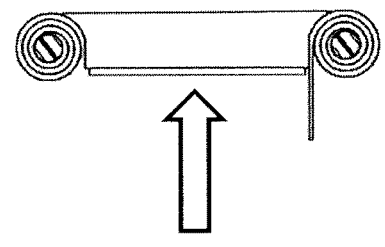

20

STERILE COVERS FOR ULTRASOUND PROBE

CROSS REFERENCE TO RELATED APPLICATIONS

This utility application claims priority under 35 U.S.C. § 119(e) of Provisional Application Ser. No. 62/097,477 filed on Dec. 29, 2014 and titled Sterile Covers for Ultrasound Probe, the entire disclosure of which is incorporated by reference herein

BACKGROUND OF THE INVENTION

This invention relates to medical devices and more particularly to ultrasound probes and devices for covering the probe for use in aseptic applications.

Ultrasound transducers are commonly used in sterile environments yet it is impractical and expensive to keep the transducers and their accompanying signal cord sterile. Sterilization is time-consuming and not performed in the area where the ultrasound equipment is used. Because ultrasound transducers are expensive, maintaining sufficient numbers of available sterilized units is cost-prohibitive. Thus, common practice is to sheath the transducer and accompanying signal cord in a sterile sheath, with the outside of the sheath being sterile and the inside of the sheath being the only part that is in contact with the non-sterile transducer and cord. A number of patents have issued in this field, including: U.S. Pat. No. 4,593,699 (a sterile cover for a sonic probe); U.S. Pat. No. 5,910,113 (telescopingly-collapsed polymeric tube with open-ended polygonal body mounted inside the tube to keep entryway of tube open, polygonal body is flat prior to use and can be popped open); U.S. Pat. No. 5,259,383 (sterile cover for ultrasound transducer and connection cable); and U.S. Pat. Nos. 7,850,664, 8,353,880 (sterile sheath for use in a biopsy system wherein biopsy needle pierces sheath). A collapsible device for single operator sheathing of an ultrasound probe is described in S. A. Lopez et al., "Design, prototyping and evaluation of a collapsible device for single-operator sheathing of ultrasound probes," Mech. Sci. 4, 1-7, 2013 doi: 10.5194/ms-4-1-2013. In a related field, a condom having deployment tabs is described in http://www.sensiscondoms.com/ All references cited herein are incorporated by reference as if fully set forth in this application.

One of the problems that a user needs to be careful of when deploying the cover is not touching the non-sterile transducer cord when unfurling the cover. It is also difficult for an individual to apply a cover to a transducer probe by themselves without a high risk of contaminating the sterile field. Most prior art approaches require either two people or something physical to hold the ultrasound probe or the cover in place while applying and deploying the cover.

Further complicating the application of the sheath to the transducer is the fact that acoustic conductive gel must be applied to the transducer head before insertion into the sheath. It is difficult for the user to access the target surface for gel application and probe insertion with current fold methods, as the cover needs to be held open with a hand and the folded portion is not compact, causing the target surface to be several inches deep inside the cover. Keeping the gel, which is non-sterile, out of contact with the practitioner's hands, while also avoiding spreading the gel to other parts of the probe and the cord is a difficult task.

Thus, a need exists for a sheath and that can be easily applied to an ultrasound probe to achieve an easily repeatable process that maintains sterility of the outside of the sheath and the gloved hands of the practitioner who installs the sheath on the probe. The present invention addresses that need by providing three embodiments of a sheath that can be applied by one person easily and without risk of loss of sterility to the outside of the sheath.

SUMMARY OF THE INVENTION

One aspect of this invention is a ring sheath applicator with self-deploying elastic bands.

A second aspect of this invention is a semi-rigid sheath holder in which the flexible sheath is housed prior to use and from which it is dispensed.

A third aspect of this invention is a doubled over rolled flexible sheath.

DESCRIPTION OF THE DRAWINGS

FIG. 17a is a partial cross section view of an exemplary rolled sheath prior to rolling;

FIG. 17b is a further partial cross section view of an exemplary rolled sheath prior to rolling;

FIG. 17c is a partial cross section view of an exemplary rolled sheath partially rolled;

FIG. 17d is a partial cross section view of an exemplary rolled sheath;

DETAILED DESCRIPTION OF THE PREFERRED EMBODIMENTS

Figure 1:
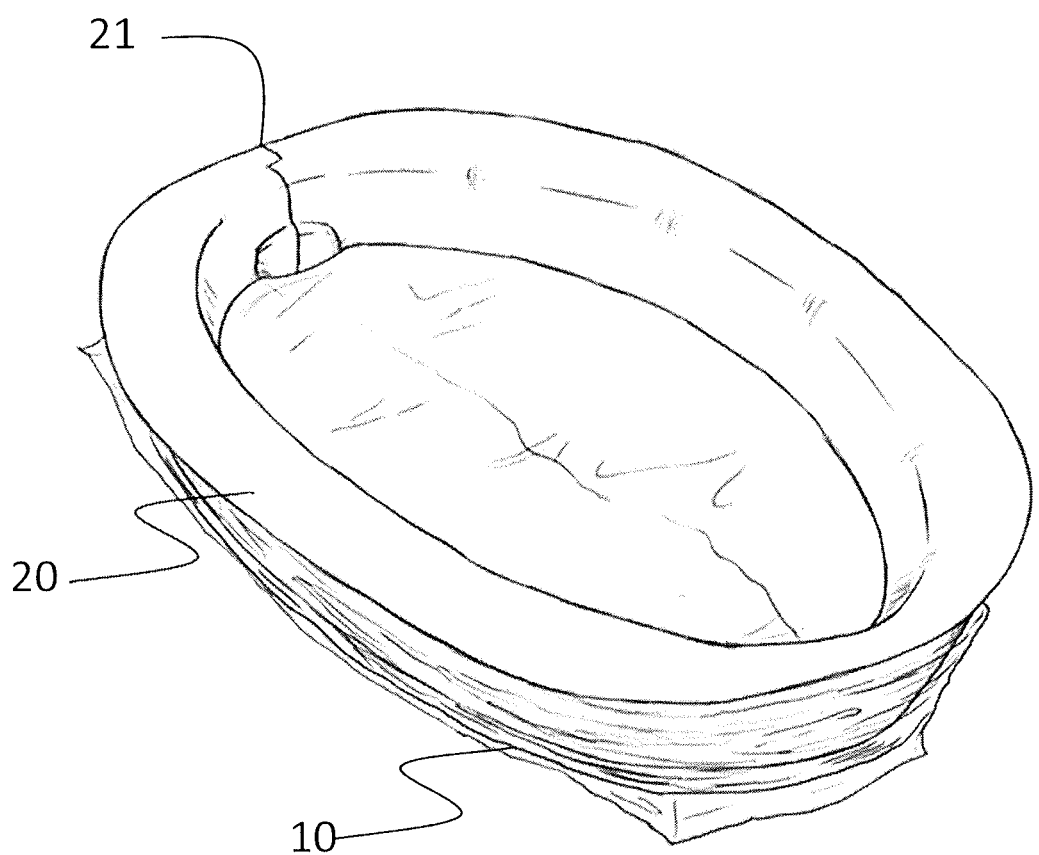
FIG. 1 is a drawing of a first embodiment of a protective sheath having a ring applicator.

Referring now to the various figures wherein like reference characters refer to like parts there are described three embodiments of the invention.

First Embodiment: Ring Applicator with Self-Deploying Elastic Bands

Figure 2:
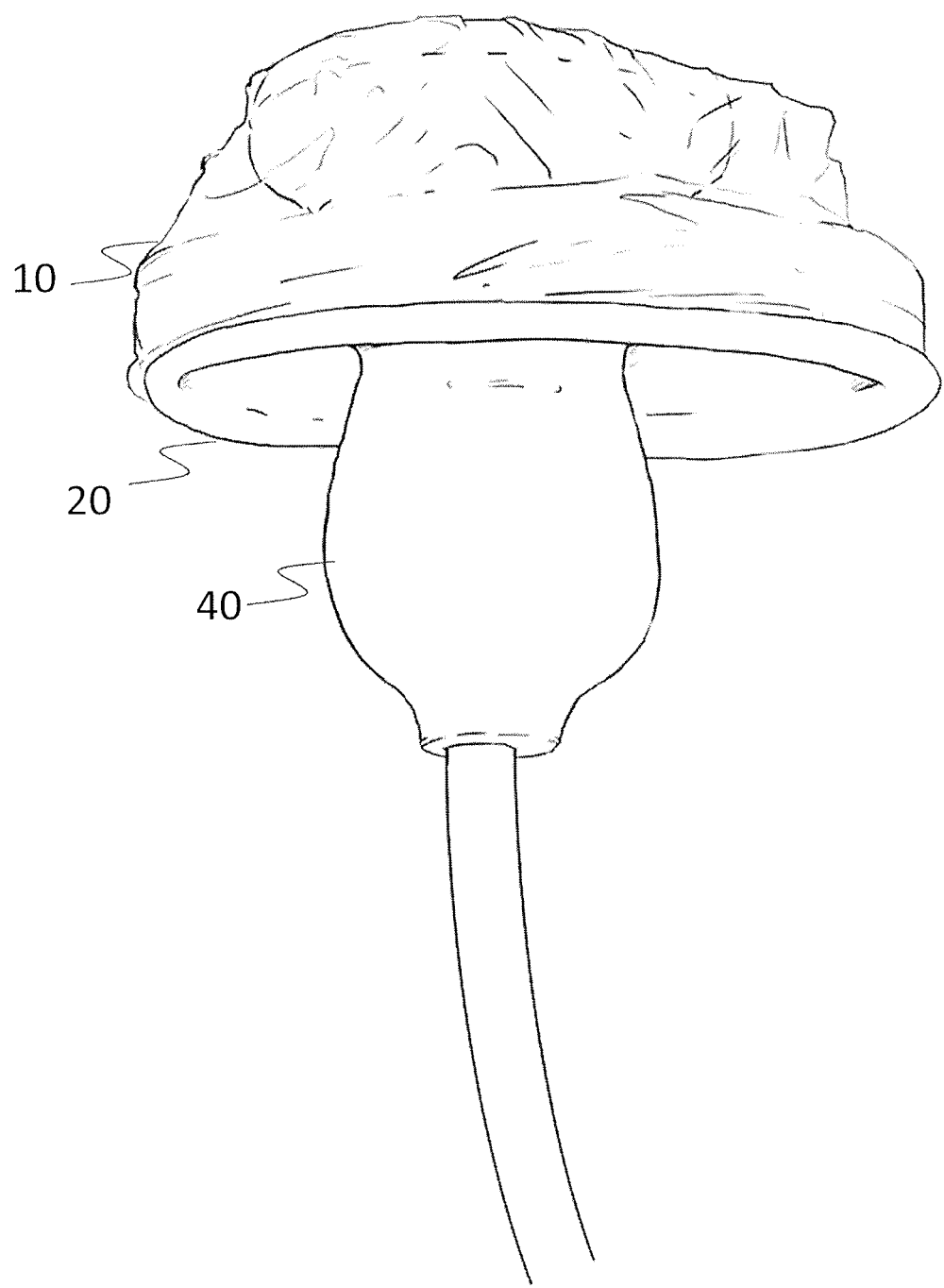
FIG. 2 a drawing of the protective sheath of FIG. 1 in a partially deployed state.
Figure 3:
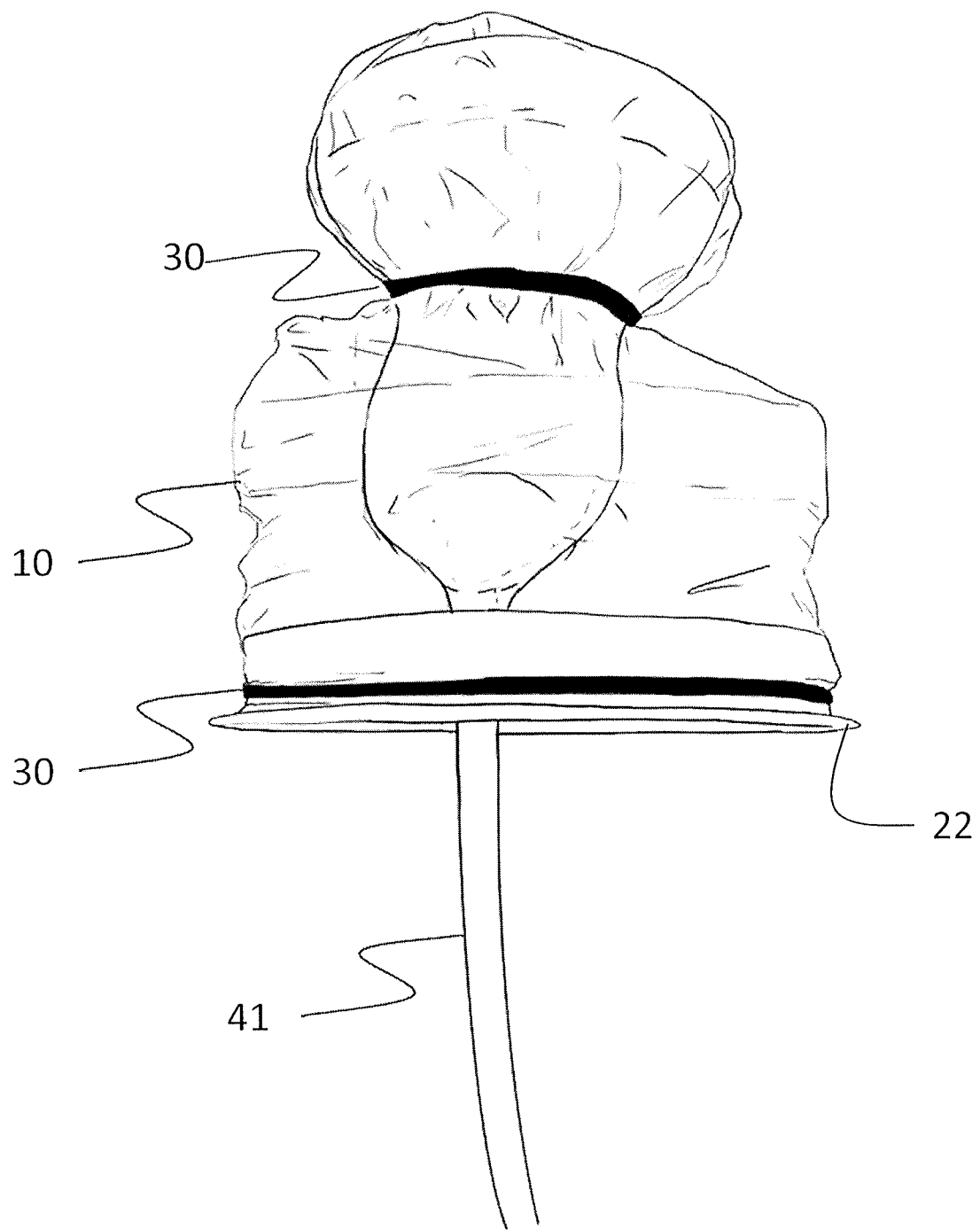
FIG. 3 a drawing of the protective sheath of FIG. 1 in a partially deployed state.
Figure 4:
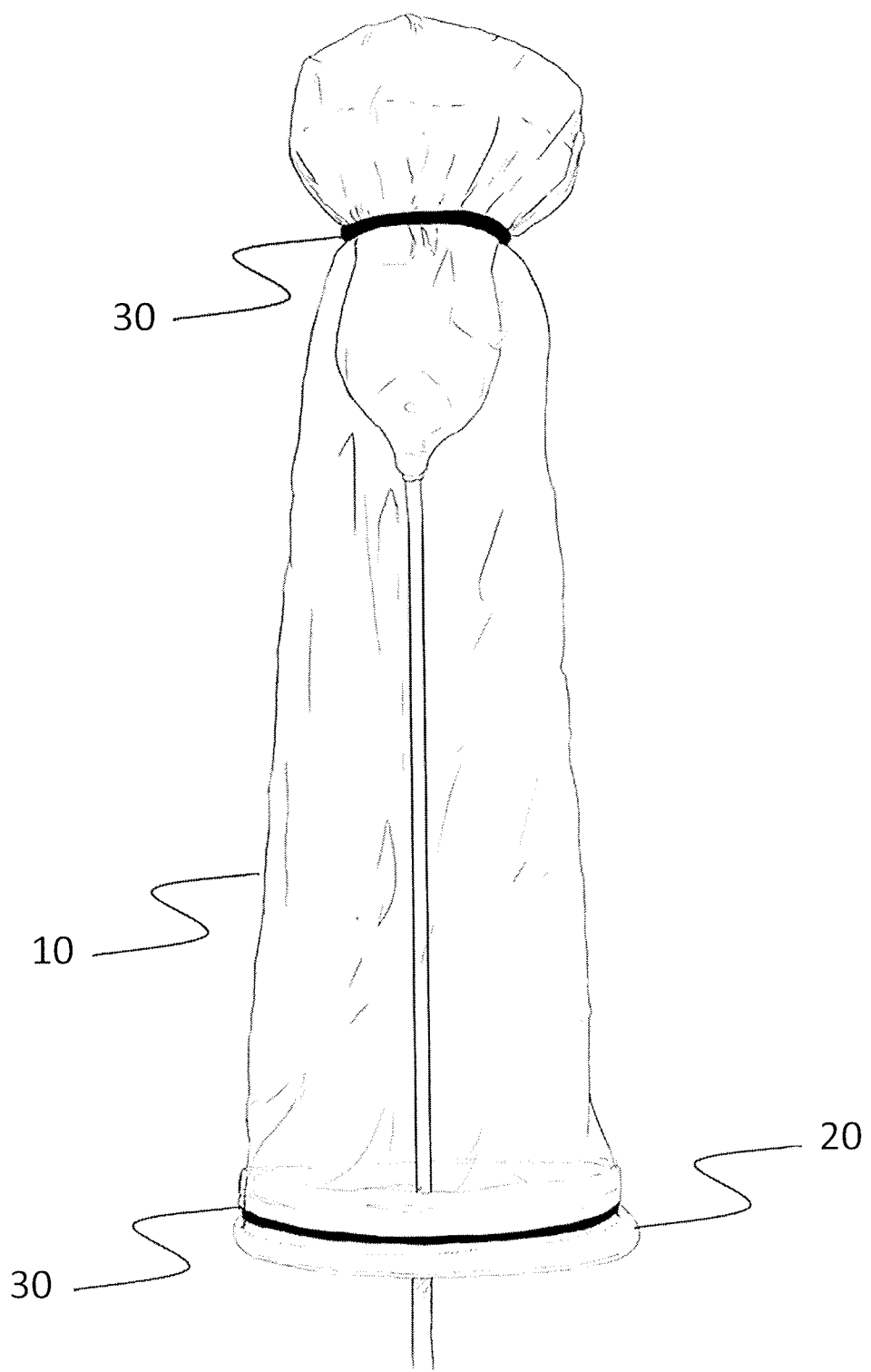
FIG. 4 a drawing of the protective sheath of FIG. 1 in a fully deployed state.

With reference to FIGS. 1-4 and 24, in this first embodiment, the cover assembly consists of a sleeve-like sheath closed on one end and open on the other end 10, a ring-shaped applicator 20, and multiple elastic bands 30. The sheath is made with traditional flexible ultrasound transducer probe cover materials and dimensions. As shown in FIG. 1, the sheath 10 is folded accordion-style along its length to be retained on the outside of the rigid applicator ring 20. The elastic bands 30 shown in FIGS. 3 and 4, are stretched around the outside of the sheath as it is placed onto the ring 20. The elastic bands are placed at intervals from the closed-end to the open-end, and drawn together within the accordion fold, helping to retain the folded sheath onto the applicator ring.

With reference to FIGS. 2 and 3, to use the inventive sheath and ring installer, an applicator ring 20, having an extended lip 22 is applied over an ultrasound transducer 40 by the user. Once the sheath is on the distal end of the transducer, the sheath-covered portion of the transducer can be grasped and the open end of the sheath pulled along the length of the transducer 40 and transducer cord 41 by holding the ring applicator and pulling away from the transducer thus causing the sheath to unfold and be transferred from the applicator to the transducer. As the sheath unfurls over the transducer, the elastic bands are transferred one-by-one to the transducer handle and cord, both releasing the sheath from the ring applicator and securing the sheath to the transducer in a form-fitting manner along its length. The ultrasound transducer and cord may be temporarily mounted on a stand that allows a practitioner wearing sterile clothing and gloves to apply the sheath without directly touching the transducer or cord.

When the full length of the sheath has been deployed, the applicator ring can be removed from the transducer cord by flexing the ring apart at break 21 and pulling the applicator free past the cord.

The ring applicator solves the problem of the difficulty for the user to access the target surface of the ultrasound transduce for gel application and probe insertion with current fold methods, as the cover needs to be held open with a hand and the folded portion is not compact, causing the target surface to be several inches deep inside the cover. The ring applicator holds the cover in a wide-open fashion and contains the folded portion in a neat and compact state, further improving the ability of a single person to apply the cover and maintain sterility, as well as improving the ease of access for gel application and probe insertion.

Figure 5:
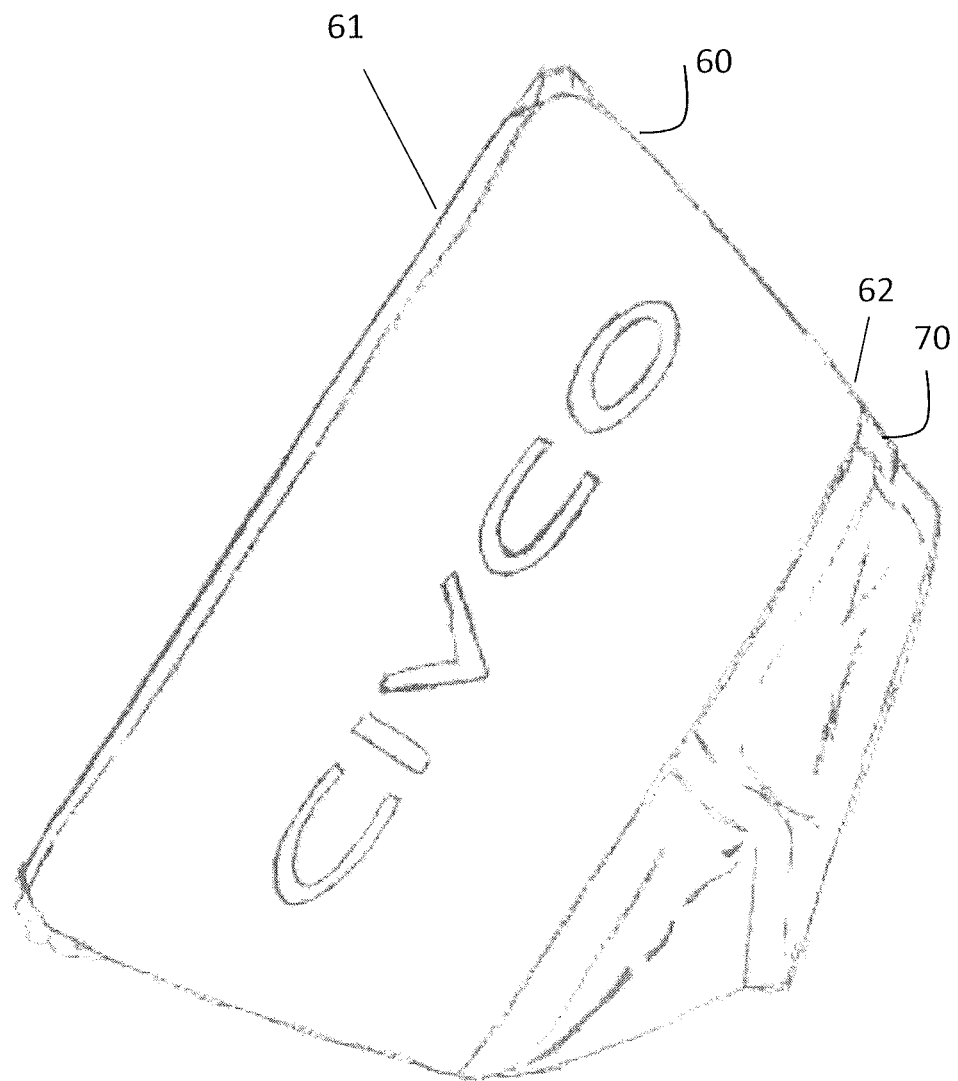
FIG. 5 is a drawing of a semi-rigid sheath dispenser with the sheath installed.
Figure 8:
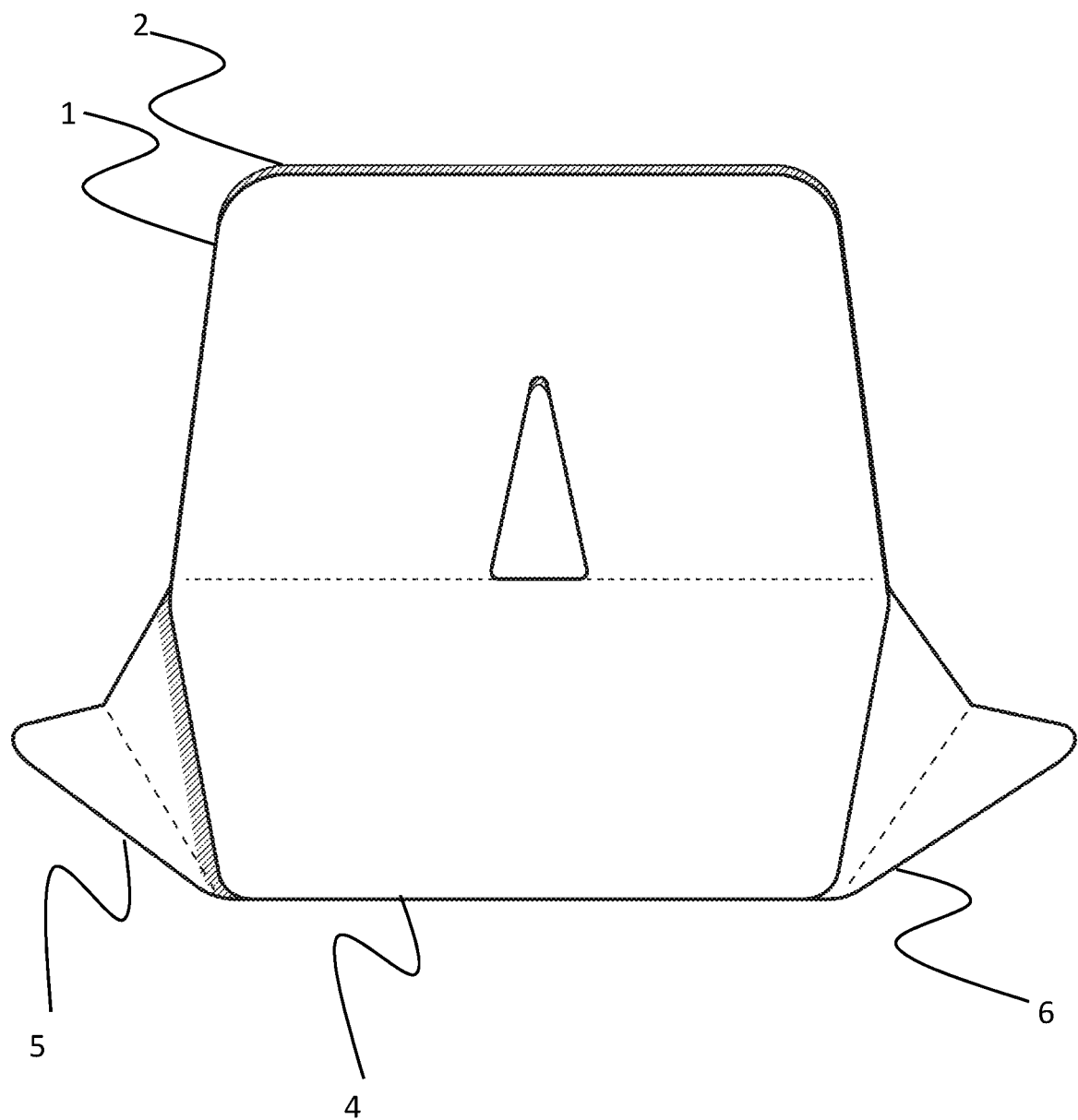
FIG. 8 is a drawing of the sheath dispenser of FIG. 5 partially assembled but without a sheath installed.
Figure 9:
FIG. 9 is a further drawing of a semi-rigid sheath dispenser with the sheath installed.
Figure 10:
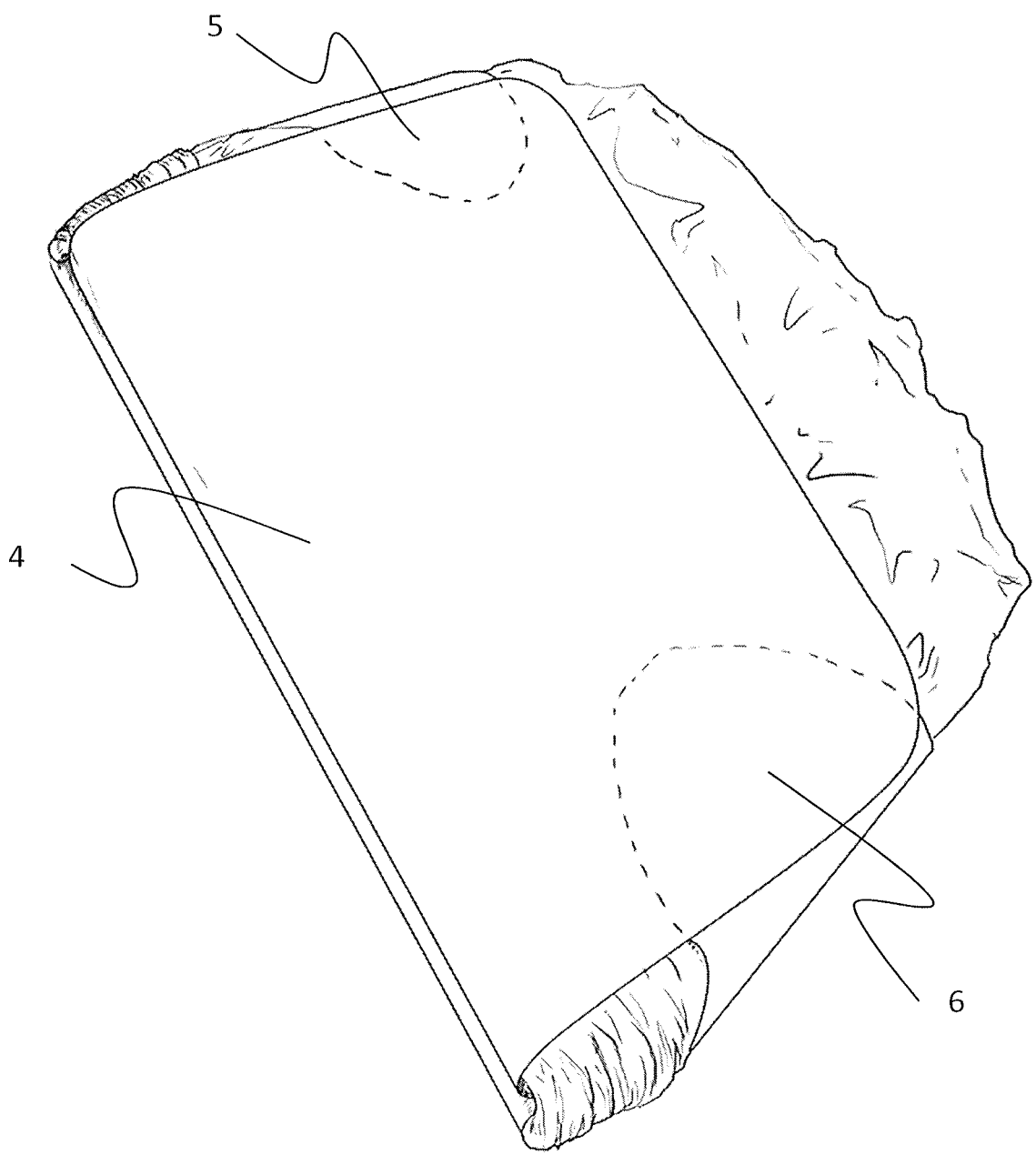
FIG. 10 is a drawing of a semi-rigid sheath dispenser with the sheath installed.
Figure 11:
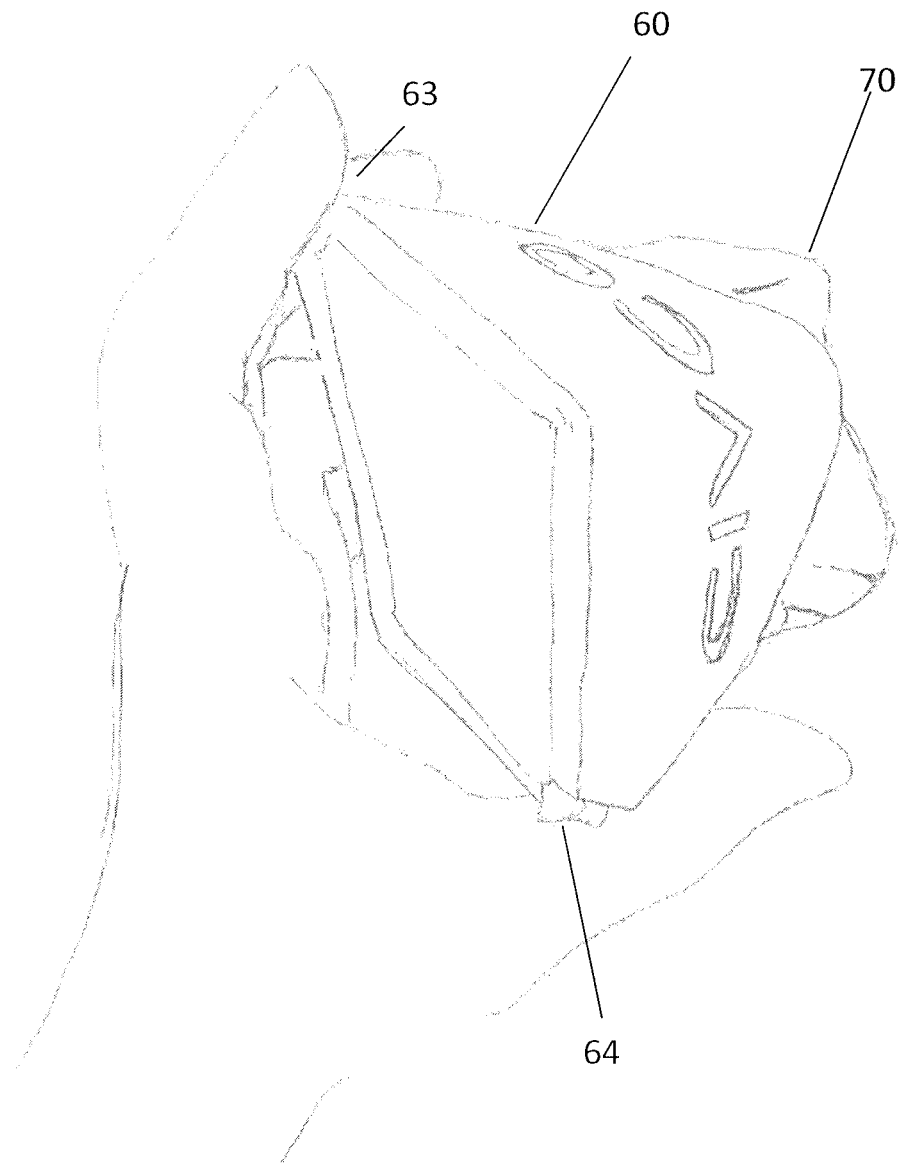
FIG. 11 a drawing of the sheath dispenser of FIGS. 5 and 10, and flexed for insertion of an ultrasound probe.
Figure 12:
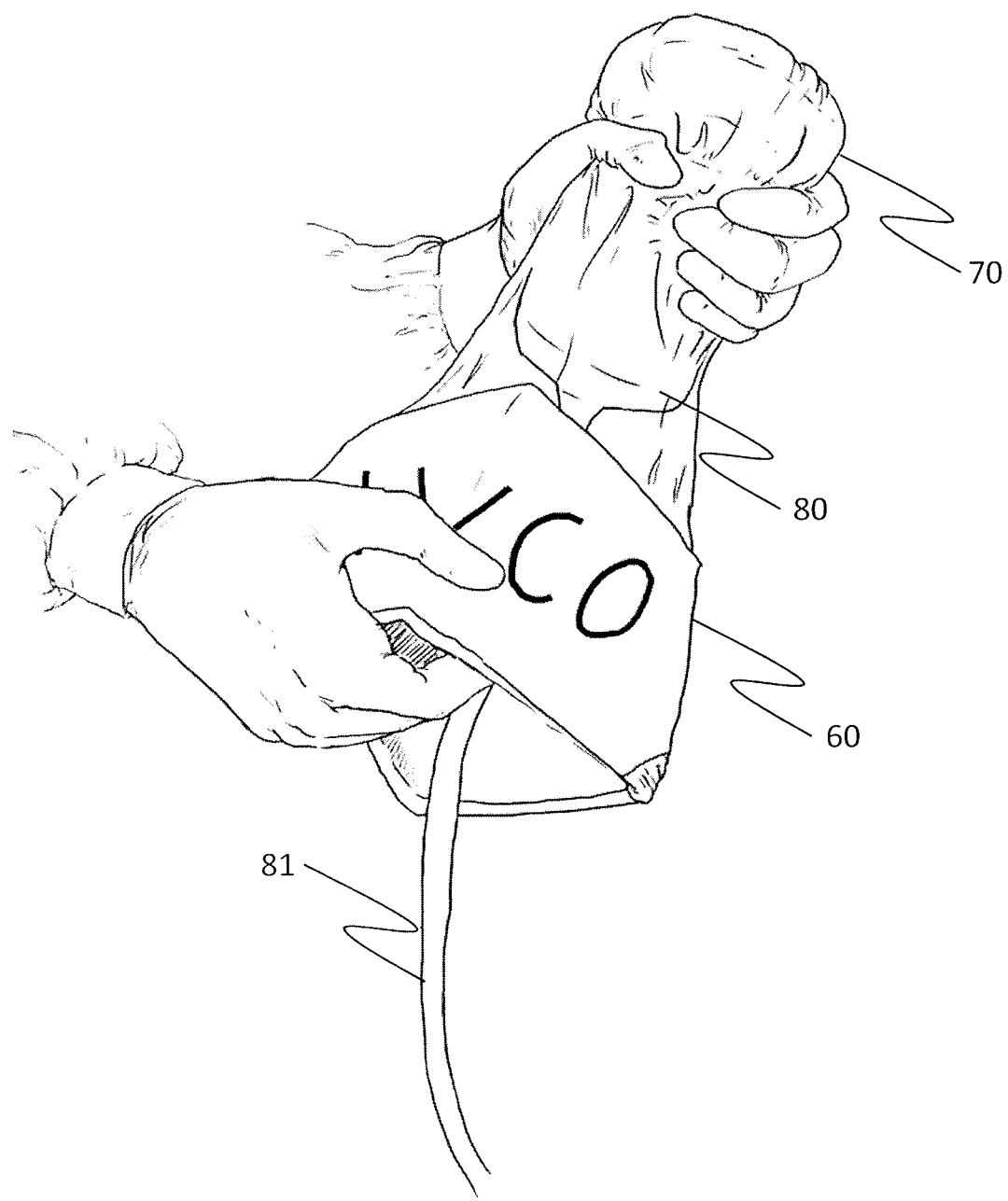
FIG. 12 is a drawing of the sheath dispenser of FIGS. 5 and 10 partially deployed over an ultrasound transducer.
Figure 13:
FIG. 13 is a further drawing of the sheath dispenser of FIGS. 5 and 10 partially deployed over an ultrasound transducer.

Second Embodiment: Semi-Rigid Two-Walled Pouch Forming Protective Sheath Dispenser A second embodiment of an improved sheath for an ultrasound probe is shown in FIGS. 5-14. In this embodiment as shown in FIG. 5, a semi-rigid dual-walled pouch 60 having two open ends 61, 62 houses an accordion-pleated protective sheath 70 between the dual walls 65, 66 of the pouch. The dual walls are clearly seen in FIG. 6, which is a bottom end view of the dispenser flexed for use. In operation, the sheath is dispensed from the bottom end of the pouch as shown in FIG. 12. The pouch can be made of cardboard or plastic or any other suitable material. The pouch is designed to house the sterile sheath and to snap open as shown in FIGS. 12 and 13 when grabbed at the corners 63, 64, as shown in FIG. 13. The protective sheath can be stuffed up inside the pouch as shown in FIG. 10 such that the pouch holds/encompasses or contains the sheath prior to use.

Figure 6:
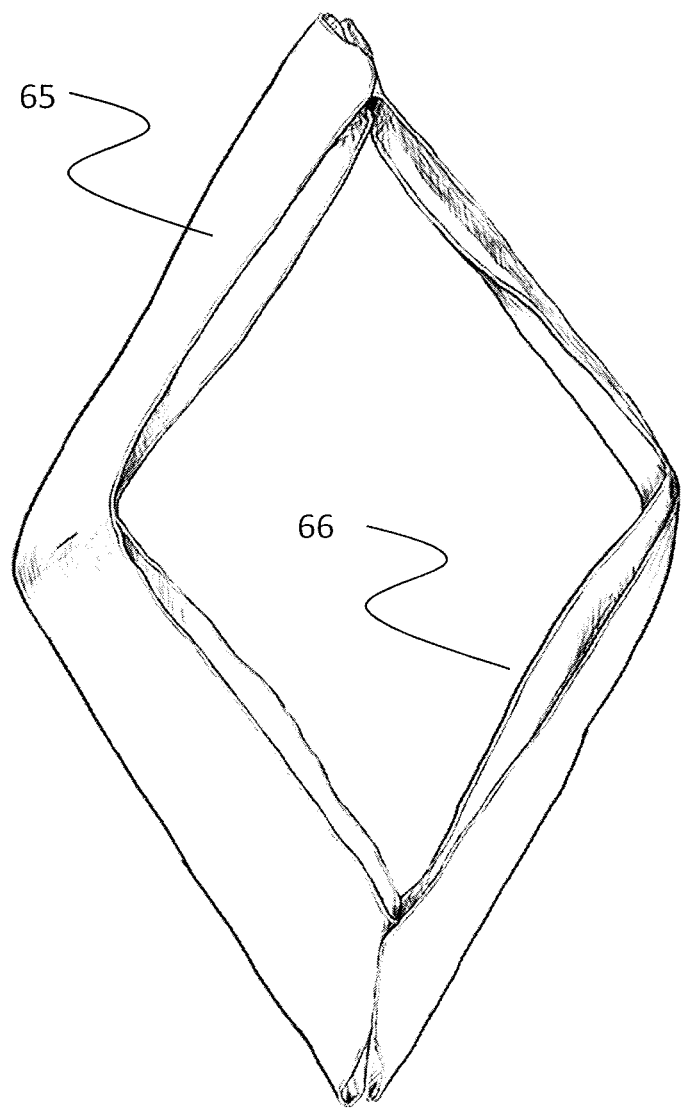
FIG. 6 is a bottom view of the sheath dispenser of FIG. 5, without the sheath installed.
Figure 7:
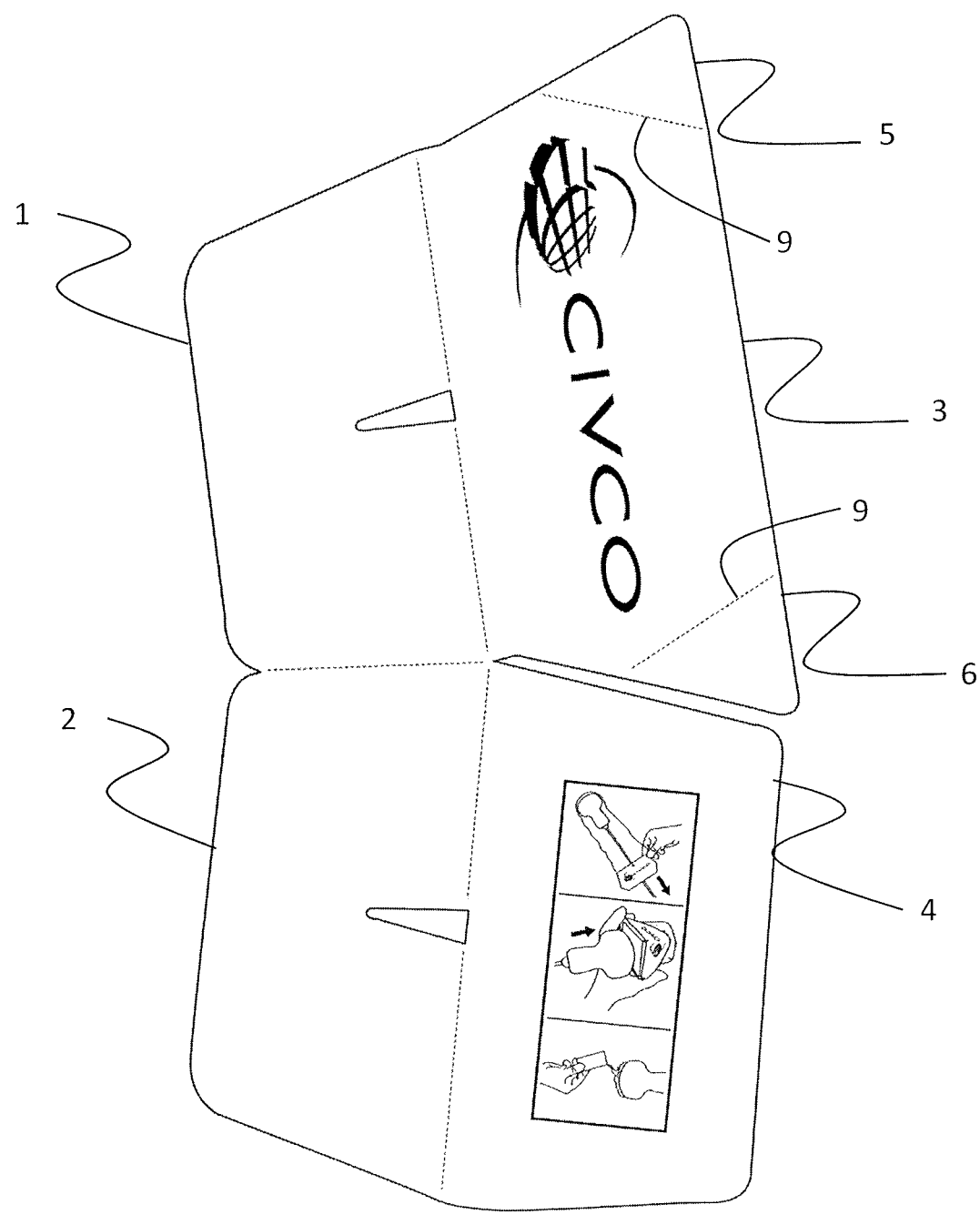
FIG. 7 is a drawing of the sheath dispenser of FIG. 5 prior to assembly.

Assembly of an exemplary dual-walled pouch is as follows: An exemplary sheet is shown in FIG. 7. The sheet of FIG. 7 is first folded between parts 1 and 2, as shown in FIG. 8 such that parts 1 and 2 end up back-to-back. Next, parts 3 and 4 are folded to a 90 degree angle from their respective adjacent portions 1 and 2, to form a base as shown in FIG. 8, where parts 1 and 2 are vertical. The vertical parts of the pouch, 1 and 2 serve as guides onto which a protective sheath 70 is slid and pushed down to form accordion-like folds as shown in FIG. 9. Once the entire sheath is pushed fully down onto parts 1 and 2 of the dispenser, parts 3 and 4 are folded up alongside parts 1 and 2 respectively to form outer walls of the dispenser. Lastly, parts 5 and 6 are wrapped around and affixed to part 4 to complete the pouch/sheath assembly. The completed pouch, without a sheath installed is shown in FIG. 6 and is shown with a sheath installed in FIGS. 5 and 10.

Advantages of the pouch design are that it uses a cost-efficient method of "folding" the cover to minimize its size. Next, the pouch provides a protective support to the cover which is beneficial in deployment of cover as well as handling the cover if deployment is performed by a single user. The cover is "folded" into a pouch type protective holder which is rigid enough to hold the cover in its "folded" configuration and makes it easier for the user to handle and use.

The method of folding the sheath into this pouch is very easy for manufacturing which makes it possible to consider for the extra cost of the pouch cover holder. The pouch also provides a printable area onto which a manufacturer's logo or use information can be printed, as shown, for example, in FIG. 7.

Figure 14:
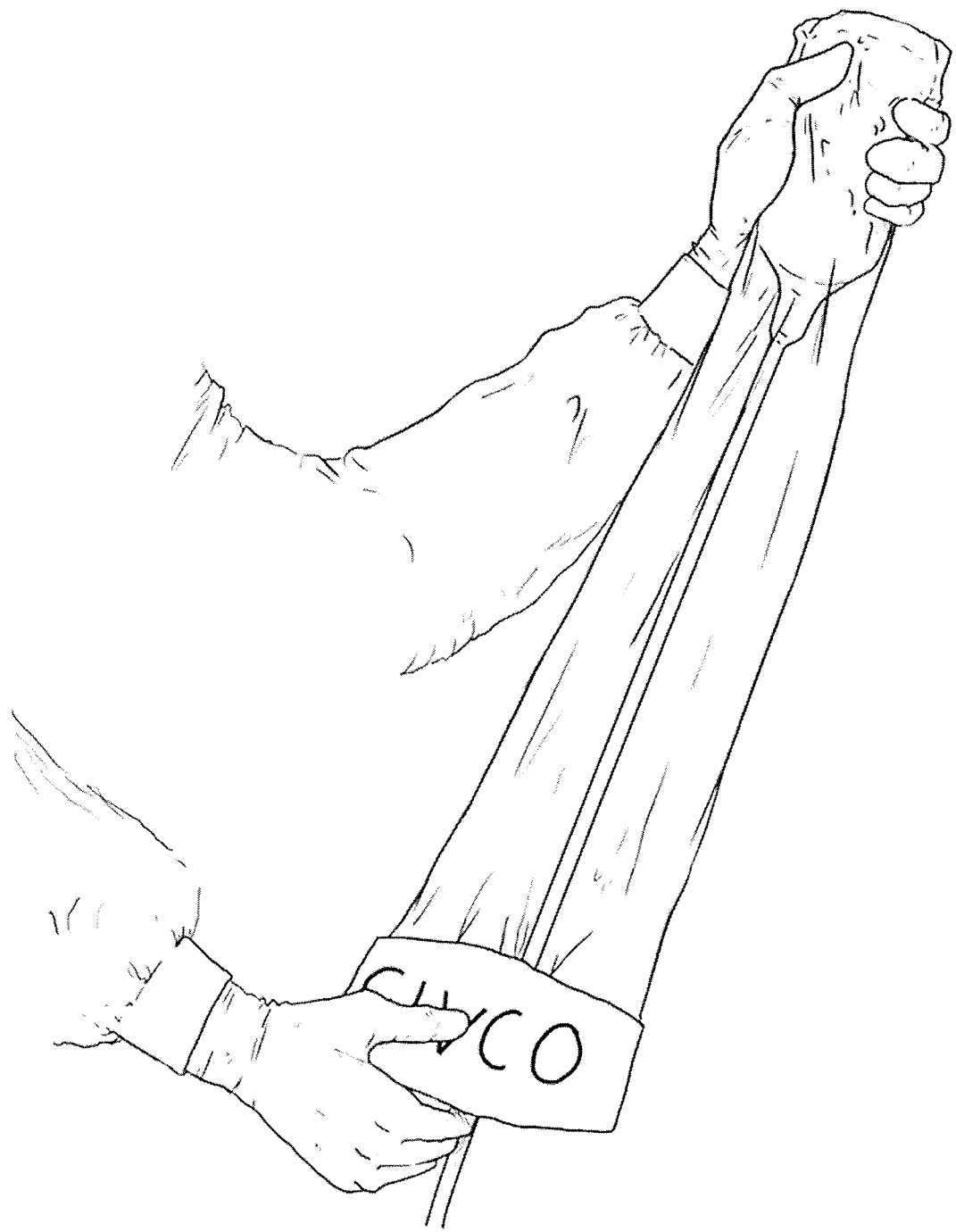
FIG. 14 is a drawing of the sheath dispenser of FIGS. 5 and 10 fully deployed over an ultrasound transducer.

Deployment of the exemplary sheath 70 out of the pouch 60 and over an ultrasound transducer 80 and cord 81 is shown in FIGS. 12-14.

Third Embodiment: Rolled Sheath

Figure 15:
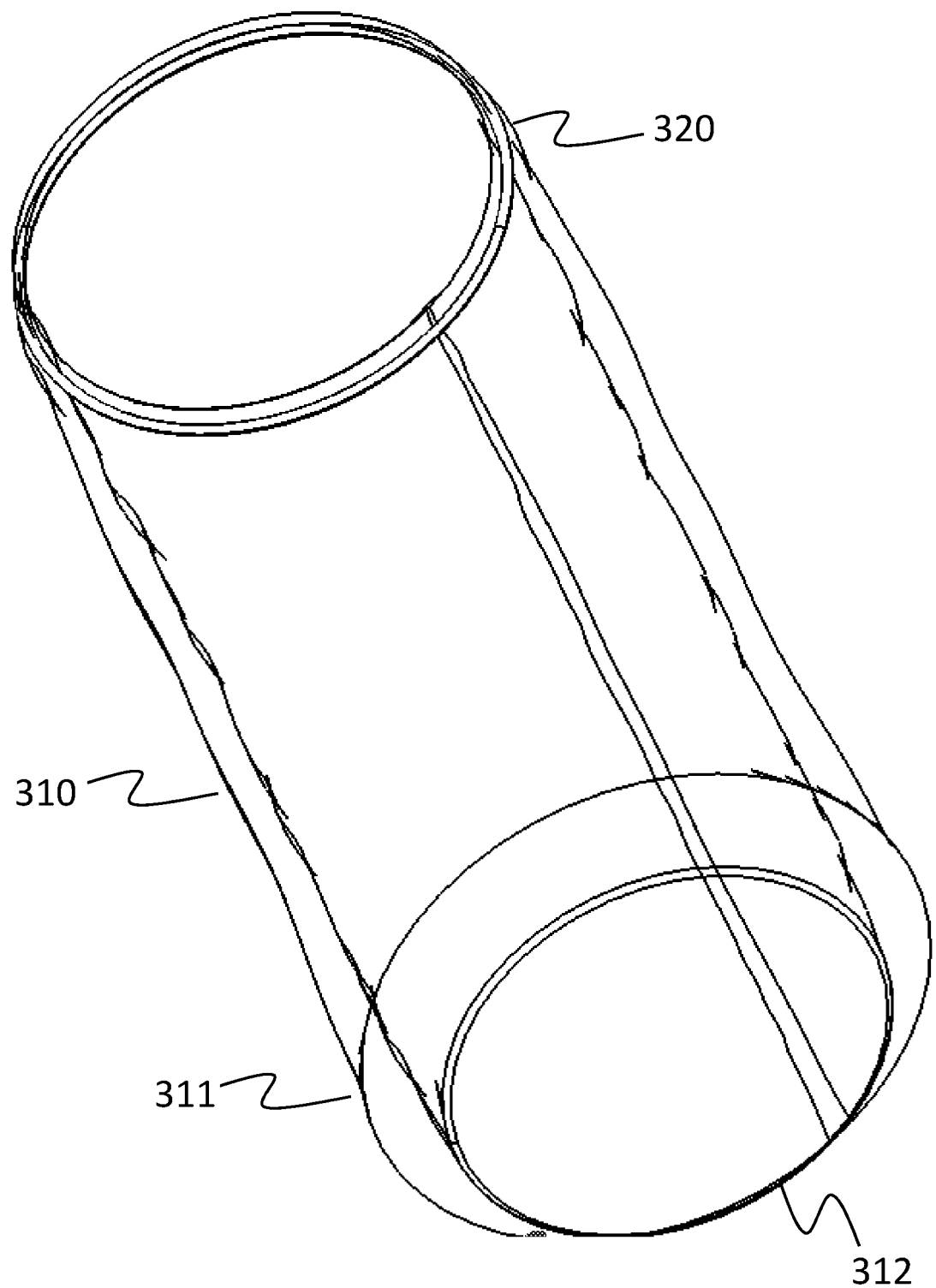
FIG. 15 is a drawing of an exemplary rolled sheath prior to rolling.
Figure 16:
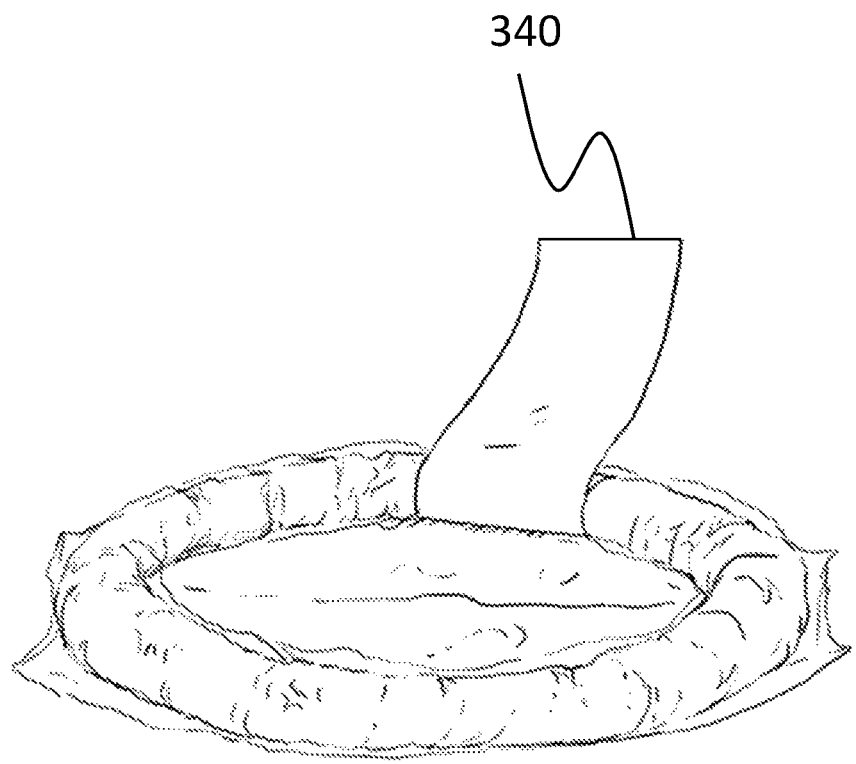
FIG. 16 is a drawing of an exemplary rolled sheath prior to use.

A third embodiment of a protective sheath for ultrasound probes is shown in FIGS. 15-23. In FIG. 15, the sheath 310 is a cylinder or other sleeve-like shaped container of flexible plastic or the like, having one open end 311 and one closed end 312. The sheath is rolled tightly around a flexible band 320, placing the folded portion in a compact state while leaving the closed end 312 that will go over the ultrasound probe fully accessible to the user. As shown in FIGS. 17a-17d, the sheath 310 is doubled over at the band, 320 such that the open end of the sheath 311 is substantially up to the closed end. This method of folding the cover is very fast and easy, and offers potential cost savings and excellent scalability for volume manufacturing.

FIG. 17a is a plan view of an exemplary cylindrical sheath having a longitudinal axis A and doubled over about its midsection at point B. The outer half of the length of the doubled over sheath is shown in full lines while the inner half of the length of the doubled over sheath is shown in hashed lines. The closed end of the sheath 312 is at the bottom of the two doubled over portions, as is the open end of the sheath, which in this view has a tab 340 attached for easy use as will be seen in the following explanation and figures. FIG. 17b shows the sheath of FIG. 17a with a flexible band 320 in cross section. FIG. 17c shows how the flexible band 320 shown in FIG. 17b is rolled down the length of the sheath, thus rolling up together both the inner and outer portions of the sheath. FIG. 17d shows a fully rolled sheath and a directional arrow pointing out the direction of insertion of an ultrasound probe.

Figure 20:
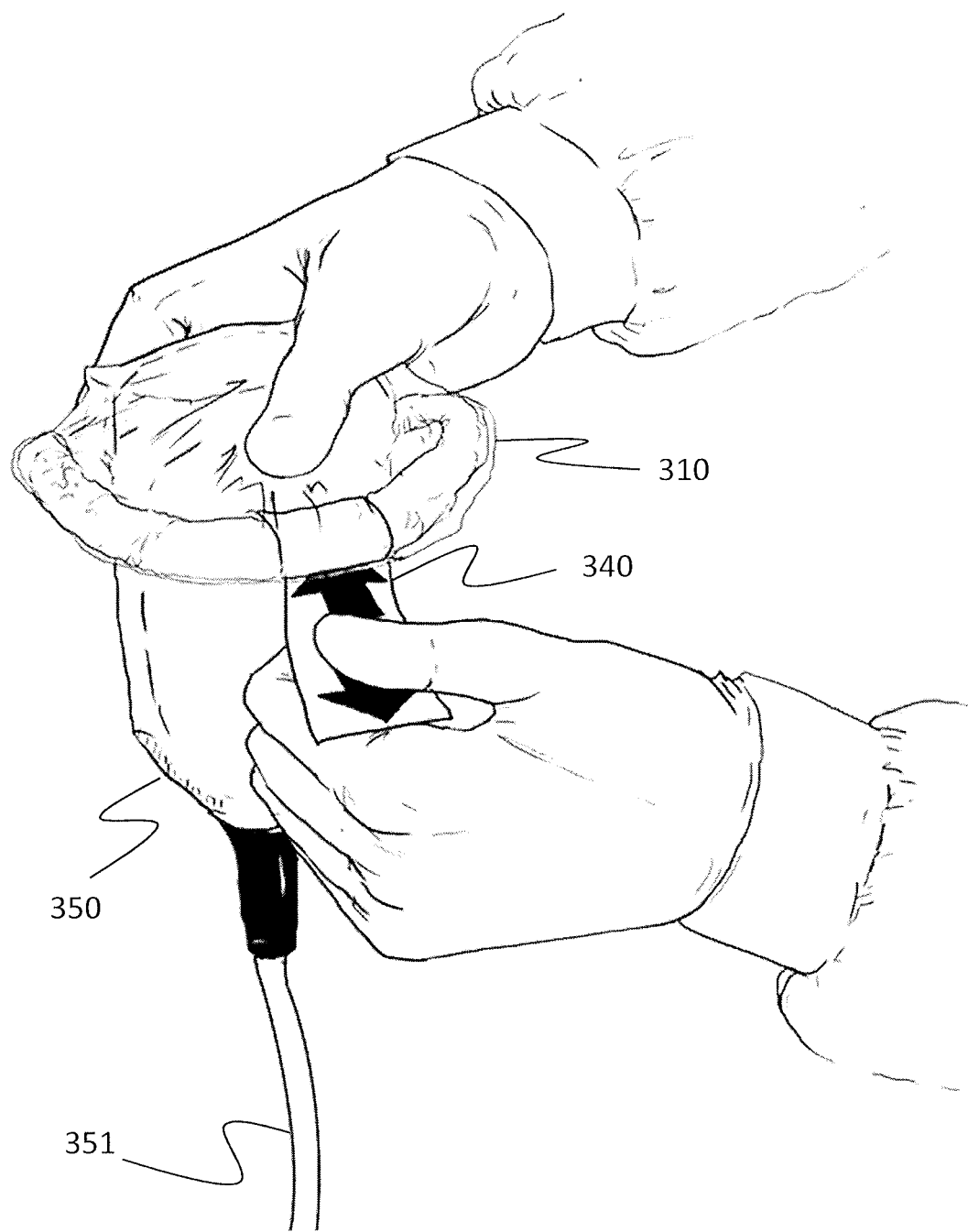
FIG. 20 is a drawing of an exemplary rolled sheath ready for application.

In a preferred embodiment, shown in use FIG. 20, one or more pull tabs 340 are attached to the open end of the rolled sheath and left exposed after the sheath is fully rolled for easy access.

Figure 18:
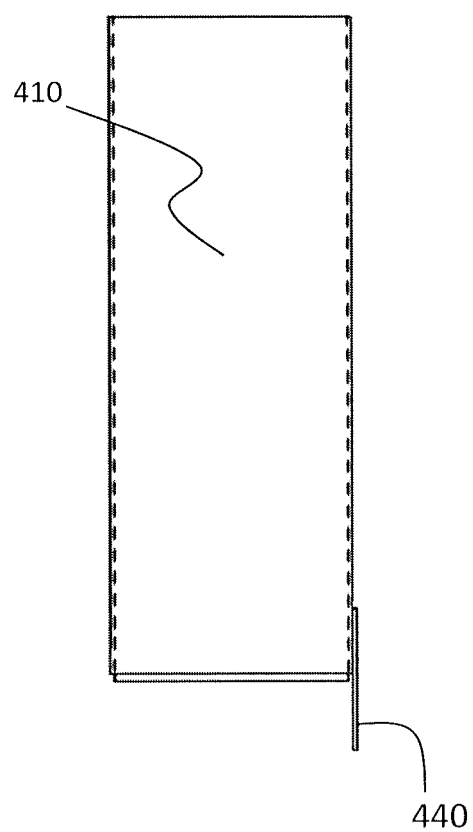
FIG. 18 is a drawing of an exemplary rolled sheath prior to being rolled.
Figure 19:
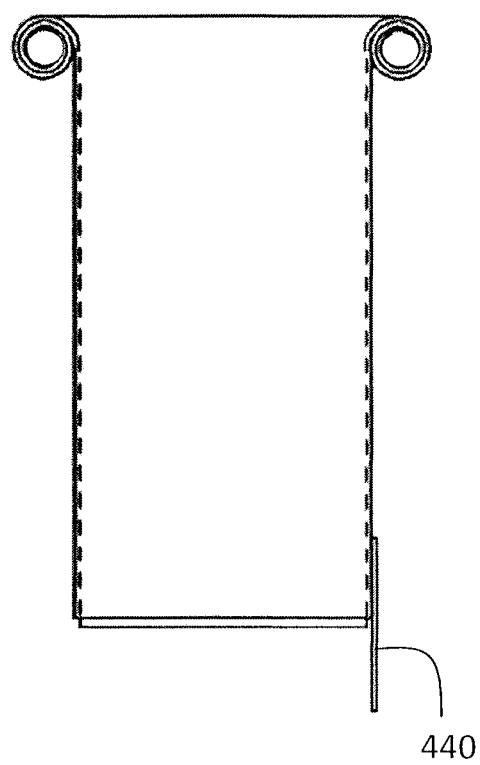
FIG. 19 is a drawing of the rolled sheath of FIG. 18 partially rolled.

As shown in FIGS. 18 and 19, a doubled over sheath 410 can also be rolled about itself without a band and can optionally include a pull tab 440 for easy deployment.

Figure 21:
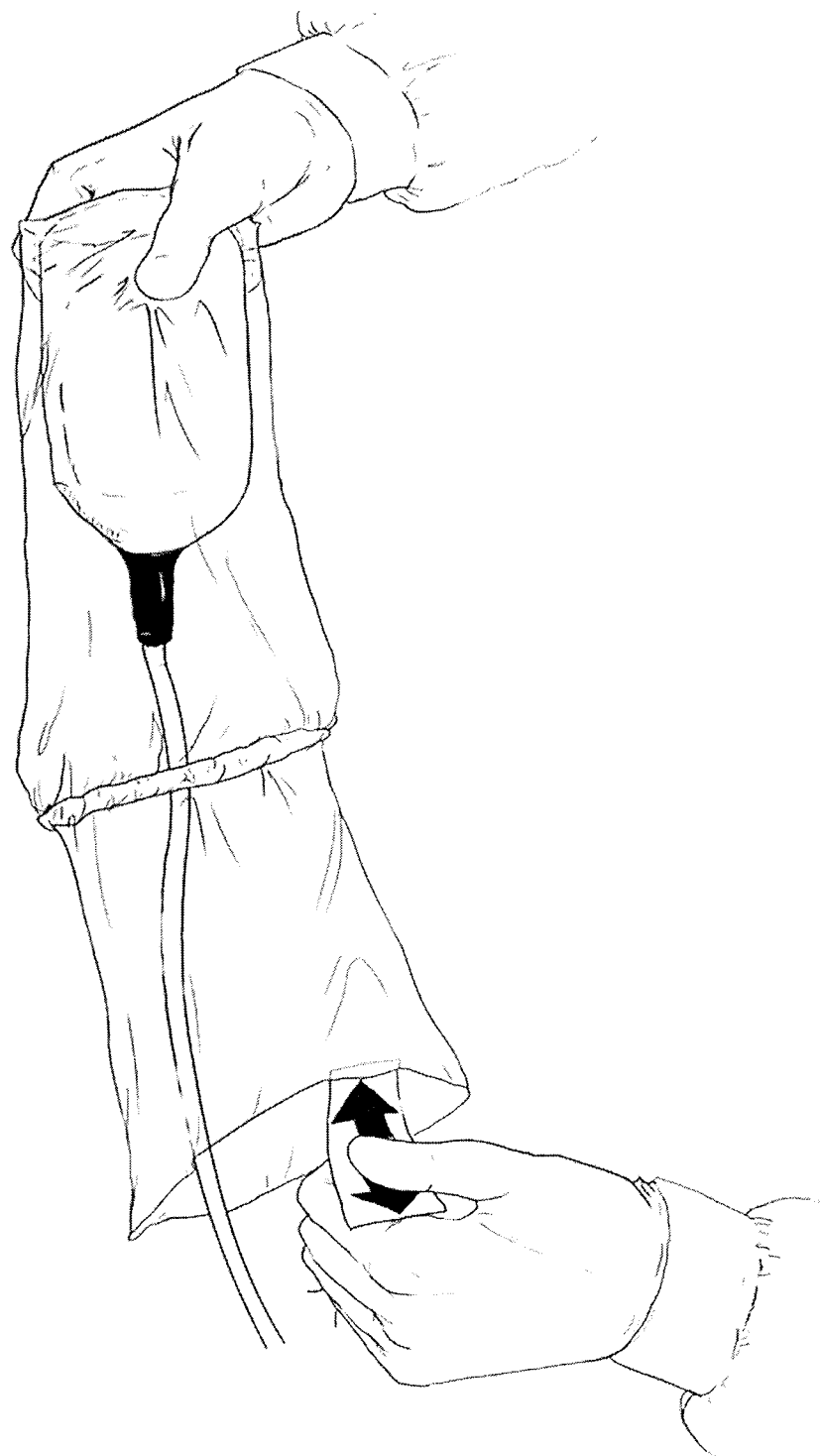
FIG. 21 is a drawing of an exemplary rolled sheath partially deployed.
Figure 22:
FIG. 22 is a drawing of an exemplary rolled sheath fully deployed.

As shown in FIGS. 20-22, the user places the sheath over the ultrasound probe 350 holding the probe through the closed end of the sheath. The user then pulls the tab 340 causing the sheath to un-roll along the length of the transducer and cord 351.

In an embodiment, the pull tab 340 can include a printed company logo, installation or expiry information.

Figure 23:
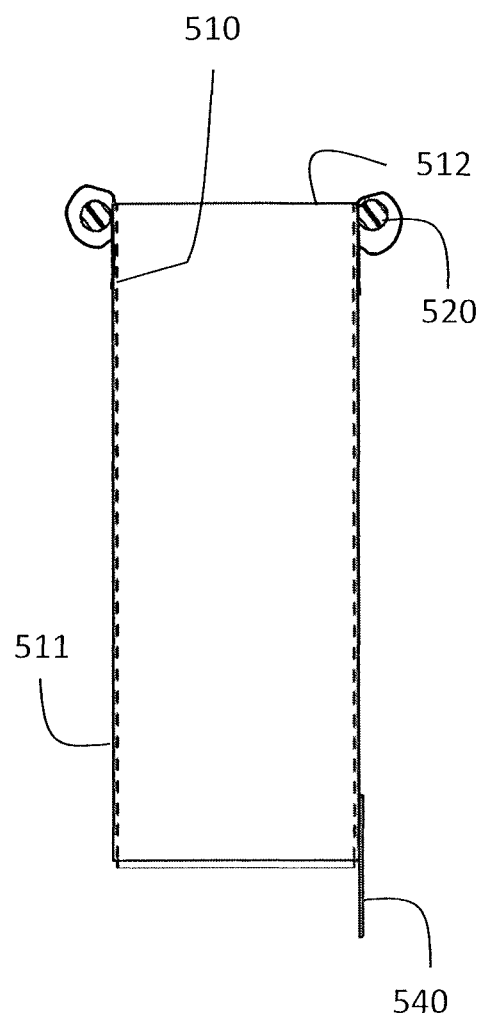
FIG. 23 is a cross section view of a further exemplary rolled sheath prior to being rolled.
Figure 24:
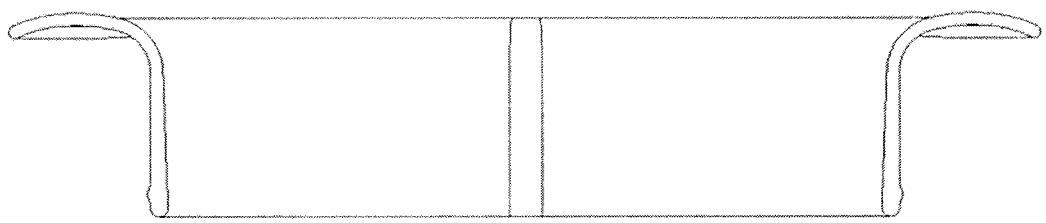
FIG. 24 is a cross section view of an exemplary embodiment of the ring applicator of FIG. 1.
Figure 25:
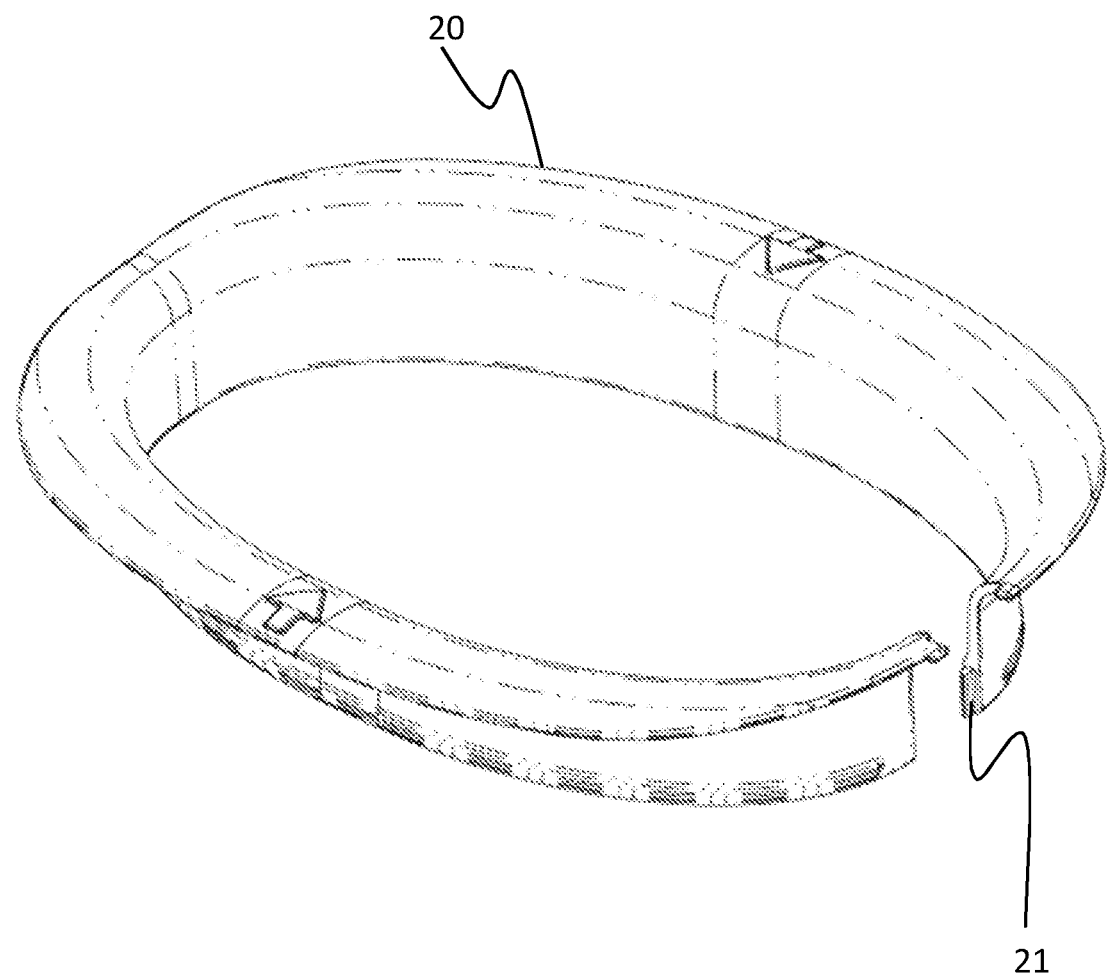
FIG. 25 is a drawing of the ring applicator of FIG. 1, shown flexed apart.

In a further embodiment, shown in FIG. 23, a band 520 is placed between the inner 510 and outer portions 511 of the folded sheath at the fold point 512. In this embodiment, the sheath is rolled as described above and can be constructed with or without a pull tab 540, as described above.

Without further elaboration the foregoing will so fully illustrate the invention that others may, by applying current or future knowledge, adopt the same for use under various conditions of service.

We claim:

1. A cover system for an ultrasound probe having a distal end portion and a proximate end portion, the system comprising:
    a cover formed of a flexible material shaped to form an elongated tubular sheath, said sheath having a longitudinal axis, an outer surface, a closed end and an open end,
    a ring applicator, and
    at least one elastic band,
    said ring applicator having an oval or circular cylindrical shape, a perimeter, distal and proximate ends and a single opening completely extending axially from said distal to said proximate end, such that the ring applicator is configured to be flexed apart about said perimeter when removed from the cover,
    said cover being applied over said ring applicator with said closed end of said cover being flush with said distal end of said ring applicator, a portion of said tubular sheath being compressed along its longitudinal axis over said ring applicator with said elastic band placed about the outer surface of said cover to hold said cover onto said ring applicator.

2. The cover system of claim 1 wherein said ring applicator further comprises a lip that extends away from said proximal end of said cylinder to aid in retaining said sheath in place prior to installation onto the ultrasound probe and to further aid in deployment the sheath.

3. The cover system of claim 1 wherein said ring applicator springs open at said open end when not restrained by said sheath and elastic band.

4. The cover system of claim 1 wherein said cover is folded accordion-style along its length on said ring applicator forming accordion folds and wherein a plurality of elastic bands are stretched around said outer surface of said cover at intervals from the closed-end to the open-end, and drawn together within the accordion folds.

* * * * *

UNITED STATES PATENT AND TRADEMARK OFFICE
CERTIFICATE OF CORRECTION

PATENT NO. : 10,799,211 B2
APPLICATION NO. : 14/982288
DATED : October 13, 2020
INVENTOR(S) : Gregory Nordgren et al.

Page 1 of 1

It is certified that error appears in the above-identified patent and that said Letters Patent is hereby corrected as shown below:

In the Claims

Column 6, Claim 2, Line 32 should read:
further aid in deployment of the sheath.

Signed and Sealed this
Twenty-second Day of December, 2020

Andrei Iancu
*Director of the United States Patent and Trademark Office*